(12) United States Patent
Wenholz et al.

(10) Patent No.: US 8,730,243 B2
(45) Date of Patent: May 20, 2014

(54) SYSTEMS, METHODS, AND USER INTERFACES FOR DISPLAYING WAVEFORM INFORMATION

(75) Inventors: Brian Wenholz, Columbia, MD (US); Wilbur Cruz Colaco, Bangalore (IN); Judy Moore, Strourbridge (GB); Karsten Russell-Wood, Baltimore, MD (US); Alistair Wood, London (GB)

(73) Assignee: General Electric Company, Schenectady, NY (US)

( * ) Notice: Subject to any disclaimer, the term of this patent is extended or adjusted under 35 U.S.C. 154(b) by 598 days.

(21) Appl. No.: 13/009,301

(22) Filed: Jan. 19, 2011

(65) Prior Publication Data
US 2012/0182301 A1 Jul. 19, 2012

(51) Int. Cl.
G09G 5/22 (2006.01)

(52) U.S. Cl.
USPC ........................................ 345/440.1; 600/523

(58) Field of Classification Search
CPC ...... G06T 11/206; A61B 5/044; A61B 5/742; G09G 1/162; G06F 11/322
USPC ......................... 345/440, 440.1; 600/523, 525
See application file for complete search history.

(56) References Cited

U.S. PATENT DOCUMENTS

| | | | |
|---|---|---|---|
| 3,752,917 A | 8/1973 | Foley et al. | |
| RE31,773 E | 12/1984 | Foley et al. | |
| 5,684,507 A * | 11/1997 | Rasnake et al. | 345/440.1 |
| 5,684,508 A * | 11/1997 | Brilman | 345/440.1 |
| 5,757,357 A | 5/1998 | Grande et al. | |
| 6,978,225 B2 | 12/2005 | Retlich et al. | |
| 7,213,009 B2 | 5/2007 | Pestotnik et al. | |
| 7,218,325 B1 * | 5/2007 | Buck | 345/440.2 |
| 7,433,827 B2 | 10/2008 | Rosenfeld et al. | |
| 2005/0021291 A1 | 1/2005 | Retlich et al. | |
| 2005/0061715 A1 | 3/2005 | Wolfgang | |
| 2007/0119505 A1 | 5/2007 | Petrenko | |
| 2009/0054797 A1 | 2/2009 | Miller et al. | |

FOREIGN PATENT DOCUMENTS

| | | | |
|---|---|---|---|
| EP | 1406198 A2 | 4/2004 | |
| EP | 1852060 A1 | 11/2007 | |
| EP | 1852065 A1 | 11/2007 | |
| EP | 2056220 A1 * | 5/2009 | |
| WO | 9535059 A1 | 12/1995 | |

OTHER PUBLICATIONS

Search Report from corresponding GB Application No. 1200728.2, dated May 16, 2012.
Unofficial Translation of Search Report and Written Opinion from NL Patent Application 2008127 dated Jul. 17, 2013.

* cited by examiner

*Primary Examiner* — Jeffery A Brier
(74) *Attorney, Agent, or Firm* — The Small Patent Law Group; Dean D. Small (57) ABSTRACT

A system for displaying physiological information. The system includes a graph module that is configured to provide a two-dimensional virtual graph having a time dimension and a signal dimension. The virtual graph includes time indicators that are spaced along the time dimension and signal indicators that are spaced along the signal dimension. The system also includes a waveform module that is configured to obtain physiological signals as a function of time. The waveform module is configured to plot a waveform based upon the physiological signals onto the virtual graph. A user interface is configured to display the waveform and the virtual graph in a viewable area. The time and signal indicators of the virtual graph shift along the time dimension at a recording speed as the waveform is plotted. The plotted waveform has a fixed relationship with respect to the time and signal indicators and shifts at the recording speed.

18 Claims, 9 Drawing Sheets

| RECORD OF CTG INTERPRETATION | | |
|---|---|---|
| DRCBRAVADO | Assessment | Comments |
| Determine Risk | Low<br>High | |
| Contractions | ___/10 min<br>___/secs | Coordinate<br>Incoordinate<br>Hypertonic |
| Baseline RAte | ___beats per minute | Within normal limits<br>Tachycardia<br>Bradycardia<br>Rising baseline |
| Variability | ___beats per minute | Normal (>5 bpm)<br>↓Suspicious (<5bpm<40min)<br>↓Abnormal (<5bpm>40min)<br>Absent |
| Accelerations | Present (>15bpm from baseline)<br>Absent | |
| Decelerations | Absent<br><br>Present | Early<br>Variable<br>Late<br>Detail |
| Overall assessment and action plan | | |
| Signature | 1. | 2. |
| Date and time | | |

SYSTEMS, METHODS, AND USER INTERFACES FOR DISPLAYING WAVEFORM INFORMATION

BACKGROUND OF THE INVENTION

The subject matter herein relates generally to systems and methods for displaying data, and more particularly, to systems and methods for displaying waveform information.

Conventional systems for displaying physiological information may be used to monitor physiological characteristics of an individual in real-time. For example, such systems may be used in cardiotocography, electrocardiography, electroencephalography, electromyography, electronystagmography, and polygraphy (i.e., lie detection). Similar systems may also be used to display seismic activity. The systems typically include a roll of strip paper having a pattern of visual indicators (e.g., gridlines), a writing system that makes traces along the strip of paper, and sensors that are connected to the writing system. The sensors may be, for example, attached to an individual at predetermined locations of the body. As the paper is rolled out at a predetermined speed, the writing system makes traces onto the paper that are indicative of the detected signals obtained through the sensors. The visual indicators, the predetermined speed, and the traces may be in accordance with established standards so that a user may quickly review and analyze the information.

However, in some cases, it may be necessary for the system to produce and for the user to review a significant amount of paper. For example, it may be necessary for a clinician to review approximately one meter of paper of a cardiotocograph to analyze conditions during pregnancy. This large amount of paper may be costly and difficult to manage. Thus, it may be desirable to provide the information through a digital viewer or display without the production of paper. However, it may be difficult to analyze information displayed in such digital viewers.

BRIEF DESCRIPTION OF THE INVENTION

In one embodiment, a system for displaying physiological information is provided. The system includes a user interface that has a viewable area that is configured to display physiological information of an individual. The system also includes a graph module that is configured to provide a two-dimensional virtual graph having a time dimension and a signal dimension. The virtual graph includes time indicators that are spaced along the time dimension indicating time intervals and signal indicators that are spaced along the signal dimension indicating a predetermined signal scaling. The system also includes a waveform module that is configured to obtain physiological signals as a function of time. The waveform module is configured to plot a waveform that is based upon the physiological signals onto the virtual graph. The user interface is configured to display the waveform and the virtual graph in the viewable area. The time and signal indicators of the virtual graph shift along the time dimension in the viewable area at a recording speed as the waveform is plotted. The plotted waveform has a fixed relationship with respect to the time and signal indicators and shifts at the recording speed.

In another embodiment, a method for displaying waveform information is provided. The method includes obtaining waveform signals as a function of time and plotting a waveform based on the waveform signals onto a two-dimensional virtual graph having a time dimension and a signal dimension. The virtual graph includes time indicators that are spaced along the time dimension indicating time intervals and signal indicators that are spaced along the signal dimension indicating a predetermined signal scaling. The method also includes displaying the virtual graph and the plotted waveform in a viewable area of a user interface. The visual indicators of the virtual graph shift along the viewable area at a recording speed as the waveform is plotted. The plotted waveform has a fixed relationship with respect to the time and signal indicators and shifts at the recording speed.

In yet another embodiment, a method for displaying physiological information is provided. The method includes obtaining physiological signals as a function of time and plotting a waveform onto a two-dimensional virtual graph that has a time dimension and a signal dimension. The virtual graph includes visual indicators that have a predetermined pattern. The method also includes displaying the virtual graph and the plotted waveform in a viewable area of a user interface. The visual indicators of the virtual graph shift along the chart portion at a recording speed as the waveform is plotted. The plotted waveform has a fixed relationship with respect to the visual indicators and shifts at the recording speed.

DETAILED DESCRIPTION OF THE INVENTION

Exemplary embodiments that are described in detail below provide systems, methods, and user interfaces that display waveform data or information. The waveform information may relate to physiological measurements obtained from individuals, seismic measurements, or other measurements of an environment. Although the various embodiments may be described in connection with cardiotocography, the methods, systems, and user interfaces described herein are not limited to cardiotocography. By way of example only, embodiments described herein may also be used in connection with electrocardiography, electroencephalography, electromyography, electronystagmography, polygraphy (i.e., lie detection), or seismology, among others. Physiological information displayed by embodiments described herein may relate to, for example, a heart rate, body temperature, blood pressure, respiratory rate, electrical activity, or intrauterine pressure. Waveforms are typically plotted as a function of time.

Embodiments described herein may generate a virtual strip chart (VSC) that is similar to a paper strip chart used in various industries. For example, embodiments described herein may generate a virtual cardiotocograph, a virtual electrocardiograph, a virtual electroencephalograph, a virtual polygraph, a virtual electromyograph, a virtual electronystagmograph, or a virtual seismograph. The VSCs may be saved or stored in a database. As used herein, users of the systems, methods, and user interfaces described herein include doctors or clinicians, nurses, patients, researchers, or other systems. The user may review the waveform information as it is generated or the user may review a history of the waveform information.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments that "comprise," "have," or "include" an element or a plurality of elements that have a particular property may also include additional such elements that do not have that particular property. Furthermore, when an element is described as being based on a factor or parameter, the term "based on" should not be interpreted as the factor or parameter being the sole factor or parameter, but may include the possibility that the element is also based on other factors or parameters.

As used herein, each of the terms "waveform signals" and "physiological signals" may include only one type of signals or multiple types of signals. For examples, physiological signals may include physiological signals relating to a first type (e.g., fetal heart rate signals) and physiological signals relating to a second type (e.g., intrauterine pressure signals). When multiple types of waveform signals are illustrated as different waveforms, the different waveforms may be synchronized in a predetermined manner. For example, the different physiological signals may be plotted along the same time axis so that the user can correlate an event or condition associated with the first type of physiological signals to an event or condition associated with the second type of physiological signals.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., modules, processors, or memories) may be implemented in a single piece of hardware (e.g., a general purpose signal processor or random access memory, hard disk, or the like). Similarly, programs may be stand alone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

Figure 1:
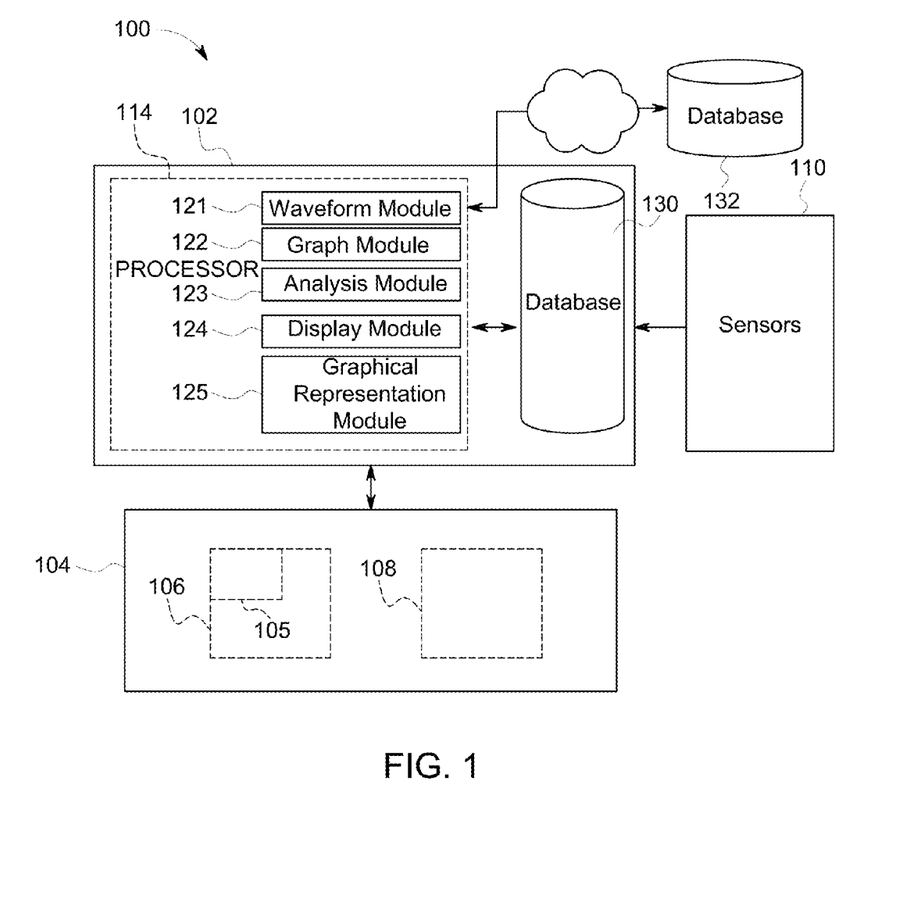
FIG. 1 is a block diagram of an exemplary system for displaying waveform information in accordance with one embodiment.

FIG. 1 is a block diagram of an exemplary system 100 for displaying waveform information or, more specifically, physiological information. The system 100 includes a computing device or system 102 that is communicatively coupled to a user interface 104. The user interface 104 may include instruments (e.g., user display), hardware, and software (or a combination thereof) that permit the system 100 to display information to the user and, in some embodiments, permit the user to provide user inputs or selections. For example, the user interface 104 may include a display 106 (e.g., monitor, screen, touchscreen, and the like) and an input device 108 (e.g., keyboard, computer mouse, touchscreen, and the like). In some embodiments, a device constituting the input device 108 may also be the device constituting the display 106 (e.g., touchscreen). The display 106 may be configured to show a viewable area that includes a viewable chart portion 105, which is described in greater detail below. The user interface 104 may also be configured to query the user and accept or receive user inputs from a user of the system 100.

The system 100 may be integrated into one component (e.g., a laptop computer) or may be several components that may or may not be located near each other. In alternative embodiments, the computing system 102 may be communicatively coupled to sensors 110 that are configured to detect measurements, such as from an individual (e.g., a patient), and communicate the measurements to the system 100 as waveform signals. In particular embodiments, the measurements are physiological measurements. The sensors 110 may be configured to detect different physiological measurements, such as a heart rate, body temperature, blood pressure, respiratory rate, electrical activity, or intrauterine pressure.

The computing system 102 may include or be part of a server system, a workstation, a desktop computer, a laptop computer, or a personal device, such as a tablet computer or a smartphone. However, the above are only examples and the computing system 102 may be other types of systems or devices. In the illustrated embodiment, the computing system 102 includes a system controller 114, which may comprise a controller, processor, or other logic-based device. The system controller 114 may have or be communicatively coupled to modules for performing methods as described herein. The modules may include a waveform module 121, a graph module 122, an analysis module 123, a display module 124, and a graphical representation module 125. Each of the modules 121-125 may be a part of another module or include another module. For example, the graphical representation module 125 may be a part of the display module 124. In addition to the above, there may be several other modules or sub-modules of the system controller 114 that are not shown. Each of the modules 121-125 may be communicatively coupled to a memory or database 130 and/or communicatively coupled to a remote memory or database 132 via, for example, the internet or other communication network. Although the database 130 is shown as being shared by the modules 121-125, each module 121-125 may have a separate memory or database.

The waveform module 121 may be configured to obtain the waveform signals. For example, the measurements detected by the sensors 110 may be transmitted to the waveform module 121. Optionally, the waveform module 121 may convert or modify the waveform signals so that the signals are recognized by other modules in the system 100 for further manipulation or analysis. For example, the waveform module 121 may identify the waveform signals as intrauterine pressure signals or fetal heart rate signals and convert or modify the physiological signals so that the signals are recognized by the other modules as corresponding to intrauterine pressure or a fetal heart rate. In other embodiments, the system 100 may be configured such that the measurements obtained through the sensors 110 are assumed to relate to certain measurements. Furthermore, in other embodiments, the user may instruct the system 100 that the signals obtained through certain sensors 110 relate to certain measurements. Also, in some cases, the waveform module 121 may receive the waveform signals from a database or another system or device. For example, the measurements may not be directly detected from a patient in real-time. Instead, the measurements may be stored and transmitted to the waveform module 121 for follow-up analysis or research.

The graph module 122 is configured to provide a two-dimensional virtual graph that facilitates visual review and analysis of the waveform signals. The virtual graph may include a clear white or beige background having visual cues or indicators patterned thereon that facilitate review and analysis. In particular embodiments, the virtual graph may include a time axis or dimension and a signal axis or dimension. The visual indicators may include time indicators that extend along the time dimension and indicate an amount of elapsed time. For example, the time indicators may be located along the time dimension at regular, predetermined intervals. Two adjacent time indicators may indicate, for example, an elapsed time of 20 seconds, 30 seconds, or one minute. By way of example only, the time indicators may be tics or vertical lines. Furthermore, the signal dimension may have signal indicators that extend along the signal dimension and indicate a value of the obtained physiological signals. The signal indicators may be located along the signal dimension at regular, predetermined intervals. The signal indicators may be tics or horizontal lines or other visual cues. In some embodiments, the graph module 122 may store different graph images.

The display module 124 may operate in conjunction with the waveform module 121, the graph module 122, and the graphical representation module 125. In some embodiments, the display module 124 may include the waveform and graph modules 121 and 122. The display module 124 may store various parameters that may be used for displaying the waveform signals. In some embodiments, the display module 124 may store various parameters that are used by established standards for displaying the physiological information. For example, the United States standard for cardiotocography has a signal range along the vertical axis of between 30 and 240 beats/minute (bpm). The U.S. scaling is 30 bpm/cm, and the recording speeds may be 1, 2, and 3 cm/min. On the other hand, the international standard for cardiotocography has a signal range along the vertical axis of between 50 and 210 bpm. The international scaling is 20 bpm/cm, and the recording speeds may also be 1, 2, and 3 cm/min.

The display module 124 may communicate the parameters with the waveform module 121 and the graph module 122 so that the waveform has the proper form (e.g., slope, peaks) and the virtual graph has the proper aspect ratio. In other embodiments, the display module 124 may modify the instructions coming from the waveform and graph modules 121 and 122 according to the parameters so that the display 106 displays the proper waveforms and virtual graphs. In some embodiments, the display module 124 may also query the user as to identify the standard to use for displaying the waveform signals and/or query the user to provide user inputs for selecting values of certain parameters (e.g., signal scaling, signal range, or recording speed).

The analysis module 123 is configured to analyze the waveform signals and identify any events-of-interest. In some embodiments, the analysis module 123 may automatically analyze the waveform signals before the waveform signals are used to generate the plotted waveform. In other embodiments, the analysis module 123 may analyze the plotted waveform generated by the waveform module 121. For example, as the system 100 receives physiological measurements from the sensors 110 that relate to intrauterine pressure and a fetal heart rate, the analysis module 123 may analyze the waveform signals directly or the plotted waveform to determine if predetermined patterns have occurred. The analysis module 123 may use one or more algorithms to identify the events-of-interest. If an event-of-interest is identified, the analysis module 123 may generate an alert or notify the user in some manner.

The graphical representation module 125 may be configured to store the various visual cues, virtual graphs, and/or waveforms during operation of the system 100. The graphical representation module 125 may also store a variety of graphical objects, such as virtual buttons or tabs. The graphical representation module 125 may also be configured to store a summary report template.

The databases 130 and 132 may store data that can be retrieved by the components or modules of the system 100 and other remotely located systems through the internet or other communication network. The databases 130 and 132 can store data that the modules 121-125 require in order to accomplish the functions of the modules 121-125. For example, the databases 130 and 132 can store the waveform signals obtained from the sensors 110.

The modules 121-125 (and the system controller 114) include one or more processors, microprocessors, controllers, microcontrollers, or other logic based devices that operate based on instructions stored on a tangible and non-transitory computer readable storage medium. For example, the modules 121-125 may be embodied in one or more processors that operate based on hardwired instructions or software applications. The databases 130 and 132 can be or include electrically erasable programmable read only memory (EEPROM), simple read only memory (ROM), programmable read only memory (PROM), erasable programmable read only memory (EPROM), FLASH memory, a hard drive, or other type of computer memory.

Figure 2:
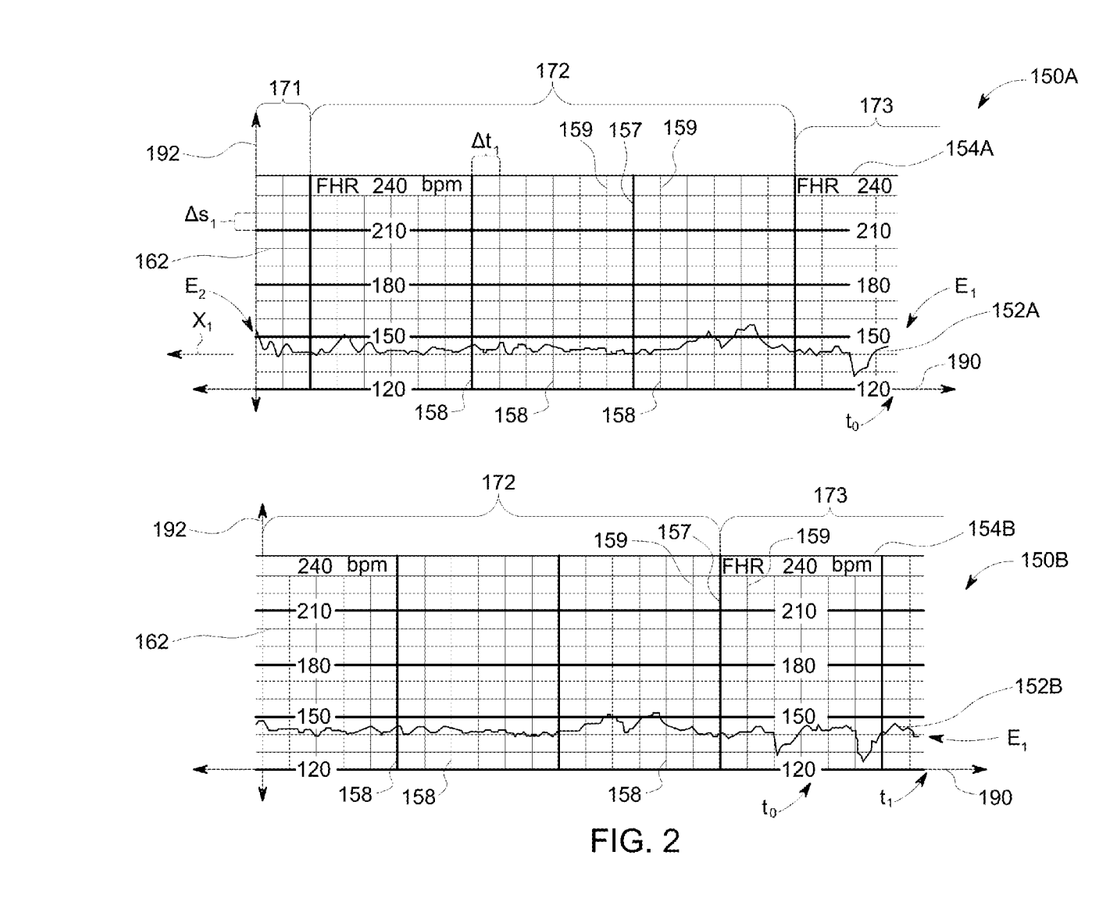
FIG. 2 illustrates a virtual strip chart (VSC) in accordance with one embodiment at two different points in time.

FIG. 2 illustrates a virtual strip chart (VSC) 150 at a time $t_0$ (indicated by reference numeral 150A) and at a later time $t_1$ (indicated by reference numeral 150B). The VSC 150 may be displayed by the user interface 104 (FIG. 1). The VSC 150 includes a virtual graph 154 and a waveform 152. (For illustrative purposes, the virtual graph 154 at times $t_0$ and $t_1$ is referenced as 154A and 154B, respectively, and the waveform 152 at times $t_0$ and $t_1$ is referenced as 152A and 152B, respectively.) At time $t_0$, the graph module 122 (FIG. 1) may provide the virtual graph 154A to the display 106 (FIG. 1) and the waveform module 121 (FIG. 1) may provide the waveform 152A to the display 106 (FIG. 1). For example, the virtual graph 154A and the waveform 152A may be provided directly to the display 106 or may be provided to the display module 124 that, in turn, provides the virtual graph 154A and the waveform 152A to the display 106. Similarly, at time $t_1$, the graph module 122 may provide the virtual graph 154B to the display 106 and the waveform module 121 may provide the waveform 152B to the display 106.

However, it should be noted that the virtual graphs 154A and 154B and the waveforms 152A and 152B are not shown immediately after each other. For example, the waveform module 121 and the graph module 122 may provide a plurality of waveforms and virtual graphs between time $t_0$ and time $t_1$ so that the VSC 150 moves smoothly and continuously through the display 106. More specifically, the VSC 150 may appear similar to actual strip paper having traces written thereon by a writing system.

As shown, the virtual graph 154 has a time dimension or axis 190 and a signal dimension or axis 192 that extend in directions that are perpendicular to each other. The virtual graph 154 may have a pattern of visual cues or indicators that facilitate a user's analysis of the waveform 152. For example, the virtual graph 154 may include time indicators 158 along the time dimension 190. In the illustrated embodiment, time increases as the waveform 152 moves from right to left. A spacing between adjacent time indicators 158 may represent a predetermined amount of elapsed time as indicated by $\Delta t_1$. In particular embodiments, the time indicators 158 are spaced apart in regular, predetermined intervals. For example, the time that elapses between adjacent time indicators 158 may be 10 seconds (or another predetermined time period). The time indicators 158 may be grid lines that extend in a direction along the signal dimension 192 in FIG. 2, or the time indicators 158 may be other visual cues in alternative embodiments, such as dots patterned across the virtual graph 154 or tics located along the time dimension 190. Also, in particular embodiments, at least one of the time indicators 158 may be visually differentiated from the other time indicators 158. For example, as shown in FIG. 2, the time indicator 157 has a heavier or darker shading than the time indicators 159 that are adjacent to the time indicator 157. The spacing between adjacent heavier time indicators 157 indicates that a minute has elapsed.

Also shown in FIG. 2, the virtual graph 154 may include signal indicators 162 along the signal dimension 192. The signal indicators 162 may indicate a predetermined scaling. In particular embodiments, the signal indicators 162 are spaced apart in regular, predetermined intervals. For example, each subsequent signal indicator 162 may indicate an increase in 10 bpm (beats/minute) or other predetermined scaling depending upon the application of the VSC. In the illustrated embodiment, the signal indicators 162 are grid lines that extend in a horizontal direction along the time dimension 190. The vertical spacing between adjacent horizontal lines represents a predetermined amount of signal change, or $\Delta s_1$. However, the signal indicators 162 may be other visual cues in alternative embodiments, such as dots patterned across the virtual graph 154 or tics located along the signal dimension 192. In some embodiments, the signal indicators 162 may also be visually differentiated from each other as desired. Also shown in FIG. 2, the virtual graphs 154A and 154B may include reference values (e.g., 120, 150, 180, 210, 240) along the signal dimension 192.

In the illustrated embodiment, the waveform 152 includes a plurality of data points plotted on the virtual graph 154 to form a tracing. The waveform 152 may be plotted with respect to the time and signal indicators 158 and 162 of the virtual graph 154. A shape or path of the waveform 152 may be based upon the physiological signals obtained through the sensors 110, the time interval $\Delta t_1$ between adjacent time indicators 158, and the signal scaling or interval $\Delta t_1$ between the signal indicators 162. The ratio of $\Delta s_1$ to $\Delta t_1$ (or $\Delta t_1$ to $\Delta s_1$) may equal an aspect ratio of the virtual graph 154. As such, a shape or path of the waveform 152 may be based upon the obtained physiological signals and the aspect ratio of the virtual graph 154.

In some embodiments, the virtual graph 154 may comprise a plurality of graph images that are positioned relative to each other. Each of the graph images may cover at least a partial area of the chart portion 105. For example, the virtual graph 154A includes graph images 171-173 positioned side-by-side in a series. The entirety of the graph image 172 and only portions of the graph images 171 and 173 are shown in the virtual graph 154A. The virtual graph 154B includes the graph images 172 and 173 positioned side-by-side. Only portions of the graph images 172 and 173 are shown in the virtual graph 154B. In particular embodiments, the graph images 171-173 are substantially identical such that the graph module 122 stores only one graph image and repeats the graph image throughout the VSC 150. The graph images 171, 172, and 173 may be positioned so that the time indicators 158 maintain a regular, predetermined pattern to represent the regular, predetermined time intervals. As such, when the waveform 152 is plotted along the graph image 172 and subsequently along the graph image 173, the information conveyed to the user appears continuous (i.e., without interruptions or change in aspect ratio).

As time elapses and more physiological signals are obtained, the VSC 150 moves in the direction $X_1$. New data points may be plotted to extend the waveform 152. More specifically, the time and signal indicators 158 and 162 of the virtual graph 154 are configured to shift along the time dimension 190 at the recording speed. New data points may be added to the waveform 152 at a chart edge $E_1$. For example, the most recently plotted data points are added to a right side of the virtual graph 154. When a new data point is plotted at the edge $E_1$, the system 100 registers a fixed position of the new data point on the virtual graph 154 so that the new data point moves with the virtual graph 154. Each of the previously plotted data points maintains a fixed position. Thus, the plotted waveform 152 may have a fixed relationship with respect to the time and signal indicators 158 and 162 and shift at the recording speed with the time and signal indicators 158 and 162. The plotted waveform 152 may also be characterized as having a fixed relationship with respect to the virtual graph 154 and/or the graph images 171-173.

In some embodiments, the VSC 150 is configured to resemble a paper strip chart that moves through the viewable area of, e.g., computer monitor or other type of display. As such, the VSC 150 may appear to move continuously in a direction $X_1$ at a recording speed. To this end, the system 100 may be configured to generate a series of frames at a predetermined frame rate or frame frequency (60 Hz) and display each frame in the chart portion 105 of the display 106. For example, each frame in the chart portion 105 may comprise a plurality of pixels in which each pixel has an address in the chart portion 105. The addresses may be defined by coordinates (e.g., x-y coordinates) or vectors.

Similar to paper strip charts, the VSC 150 may have an operative length that corresponds to a length in time in which the physiological signals were recorded. For instance, if the patient's physiological signals were recorded for one hour and the recording speed was 3 cm/minute, then the operative length of the paper strip chart (and the VSC 150) would be 180 cm. However, when the physiological signals are recorded for an extended period of time, only a portion of the VSC 150 may be shown in the chart portion 105. For example, a length of the VSC 150 shown in the chart portion 105 may be approximately 12.0 cm. Thus, embodiments described herein may be configured to show a visual portion of the VSC 150 and store a remainder portion of the VSC 150. The remainder portion of the VSC 150 may then be retrieved by a user at a later time for review.

The following illustrates one example of generating a VSC 150. In some embodiments, the VSC 150 comprises a plurality of frames that are displayed at a frame frequency. For example, one frame may be similar to the VSC 150A shown in FIG. 2 at time $t_0$ and another frame may be similar to the VSC 150B at time $t_1$. For illustrative purposes only, the VSC 150 may have an operative length of 18 cm that is based upon 360 seconds of recorded physiological signals. The VSC 150 may include 360 frames or one frame for each second. However, it is understood that the VSC 150 may include more than one frame per second or less than one frame per second. In this example, the time $t_0$ may be about 235 seconds into the recordings and time $t_1$ may be about 275 seconds into the recordings. Thus, the difference between $t_0$ and $t_1$ is about 40 seconds.

As shown in FIG. 2, the frame that is represented by the VSC 150A includes the graph images 171-173 and the waveform 152A. The data points of the plotted waveform 152A may have known fixed positions with respect to the time and signal indicators 158 and 162, the graph images 171-173, and/or the virtual graph 154A. After the system 100 receives another second of physiological signals, the graph images 171-173 may be shifted a distance that represents one second (or ⅒ of $\Delta t_1$ in FIG. 2) in the direction $X_1$ and a new data point may be added to the waveform 152 proximate to the edge $E_1$. More specifically, to generate the next frame, the graph images 171-173 may be provided to the display. However, the graph images 171-173 may provided to different addresses to represent one second of movement. Thus, when the graph images 171-173 are provided for generating another frame, the system 100 is not required to recalculate each pixel that defines the corresponding graph images in the chart portion. Instead, each of the graph images 171-173 is moved as a unit. In such embodiments, the system 100 may require fewer calculations than other known imaging methods. Furthermore, as discussed above, the graph images 171-173 may be substantially identical. In such embodiments, the system 100 is only required to store and display one graph images multiple times. Again, the system 100 may require fewer calculations than other known imaging methods.

As described above, the VSC 150B is indicative of a frame at time $t_1$, which is approximately 40 seconds after the time $t_0$. In between times $t_0$ and $t_1$, a plurality of frames of the VSC 150 may be displayed at a rate of one per second. Each new frame may include a new data point at the edge $E_1$ and have an old data point removed at the edge $E_2$. However, the system 100 may store the location of the removed data points with respect to, for example, the time and signal indicators 158, 162 and/or the graph images 171-173 to facilitate retrieval of the physiological information. For example, a user may enter user inputs through the user interface 104 to request a history of the VSC 150. The user may enter the requested time period (e.g., from the beginning of recordings, the last ten minutes) to recall the history of the VSC 150 or, in embodiments where the user interface 104 includes a touchscreen, the user may slide a finger in a direction that is along the time dimension 190 to scroll through the VSC 150. When a history of the VSC 150 is recalled, the graph module 122 may display the stored graph images and the waveform module 121 may provide the plotted waveform. In some embodiments, when a user is reviewing the history of the VSC 150, the system 100 may continue to obtain the physiological signals.

Figure 3:
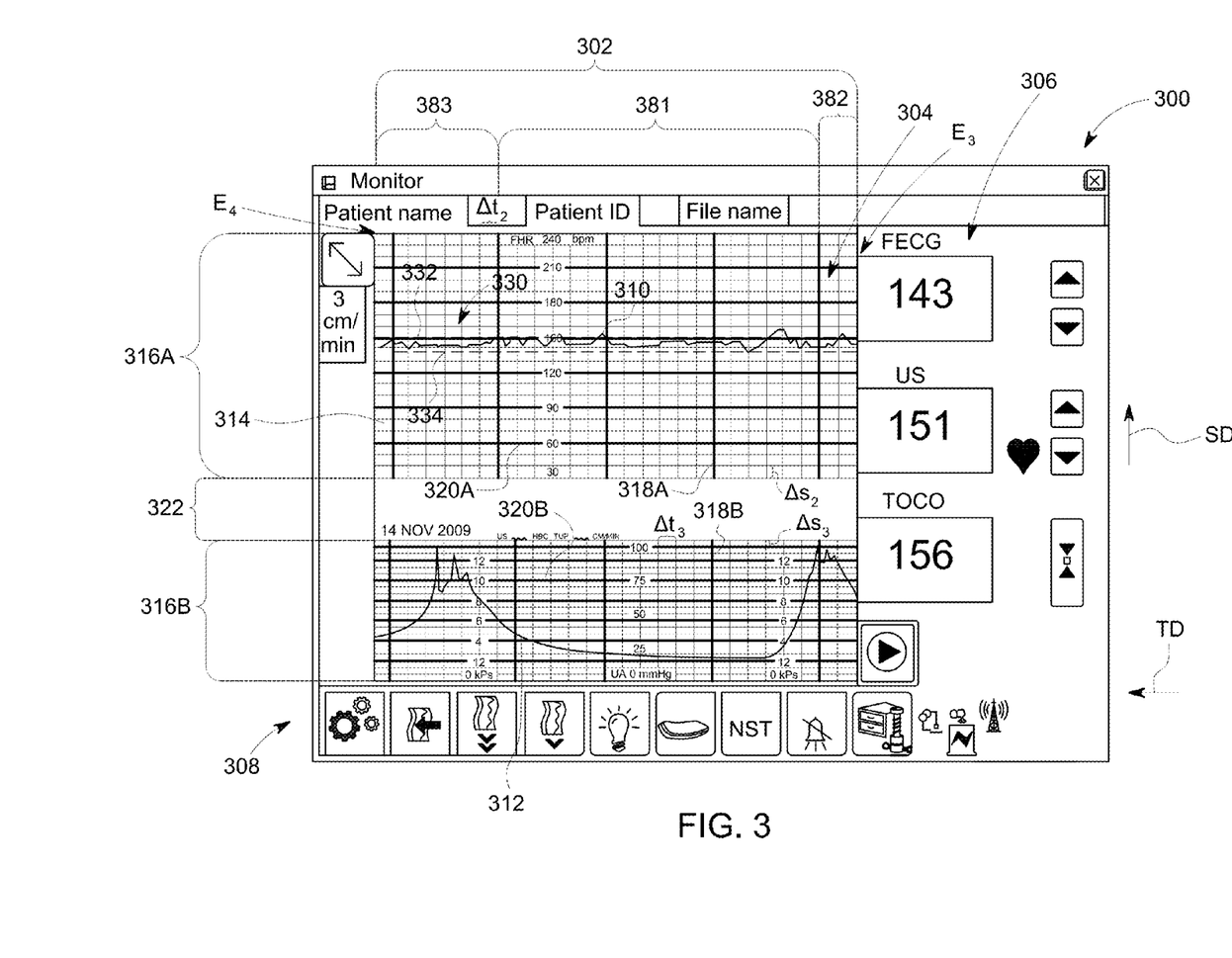
FIG. 3 shows a viewable area of a user interface according to one embodiment.
Figure 4:
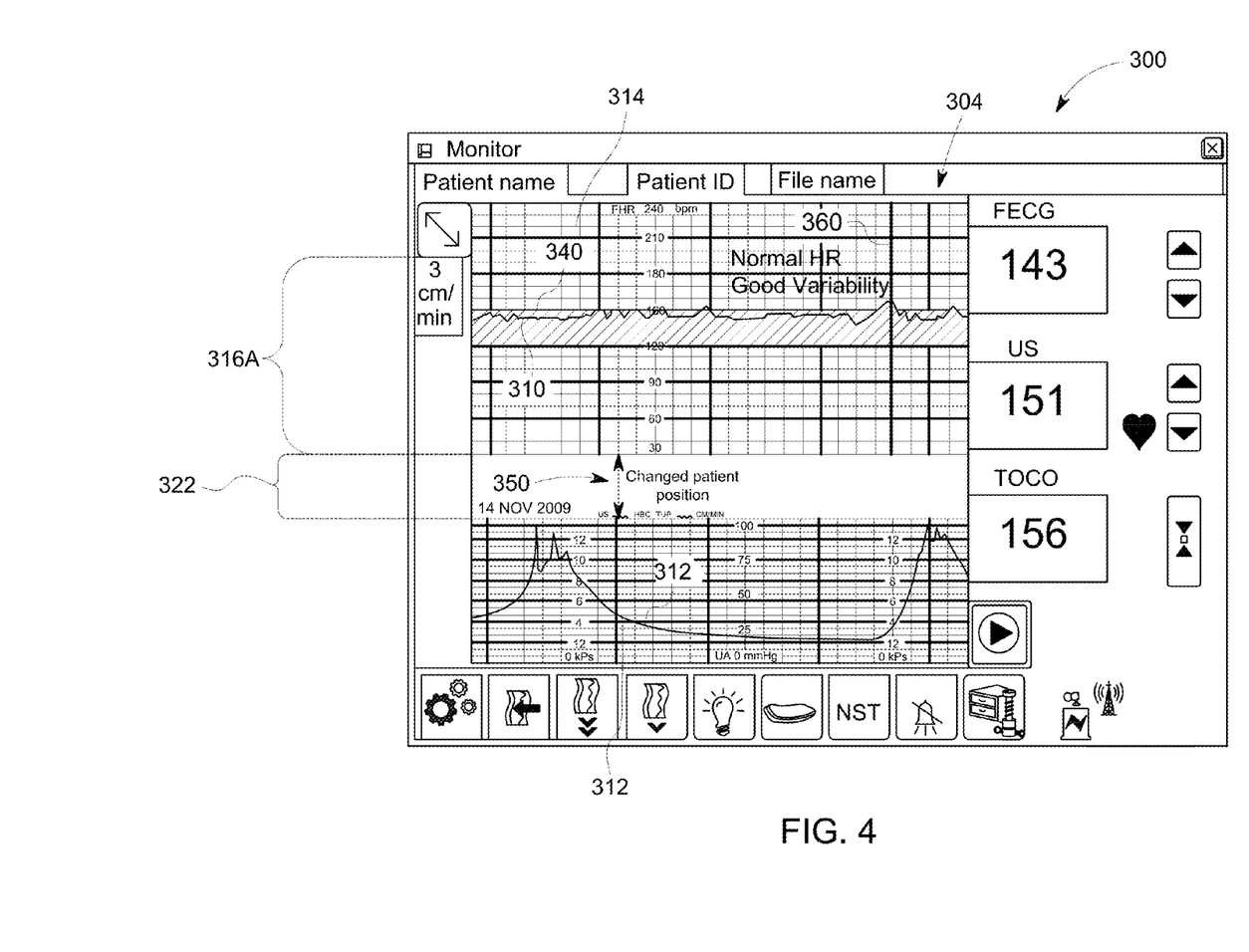
FIG. 4 shows the viewable area of FIG. 3 and illustrates user-selected annotations and a system-generated notice.
Figure 5:
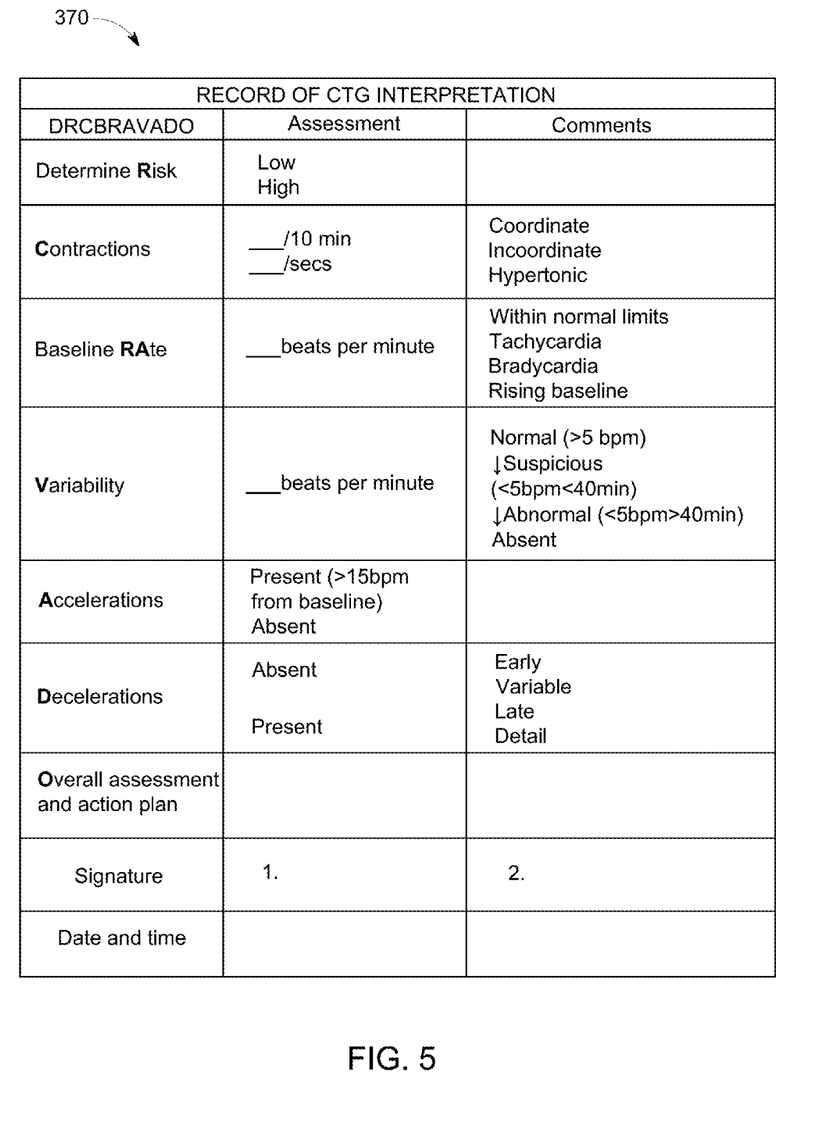
FIG. 5 shows another system-generated notice in accordance with one embodiment.

FIGS. 3-5 show a viewable area 300 of a user interface in accordance with one embodiment. The user interface may be similar to, for example, the user interface 104 (FIG. 1). As shown in FIG. 3, the viewable area 300 includes a chart section or chart portion 302 having a VSC 304 located therein. The chart portion 302 may be similar to the chart portion 105 described above. The chart portion 302 extends between chart edges $E_3$ and $E_4$. The VSC 304 may display physiological information. The viewable area 300 also includes a statistical data section 306 that extends vertically along a side of the viewable area 300 and a function or tool section 308 that extends horizontally along a bottom of the viewable area 300. The statistical data section 306 may display numbers that correspond to current measurements. For example, the statistical data section 306 may show a fetal electrocardiogram (FECG) signal that represents electrical activity of the fetal heart; an ultrasound (US) signal; and a TOCO signal that reflects uterine activity. Also shown, the viewable area 300 may display the recording speed of the VSC 304. In the illustrated embodiment, the recording speed is 3 cm/min.

Embodiments described herein may be configured to display waveform information from more than one type of measurement. As shown, the VSC 304 includes a virtual graph 314 that has a time dimension that extends in a direction TD and a signal dimension that extends in a direction SD. The virtual graph 314 has sub-graphs 316A and 316B. Each sub-graph 316A and 316B may include respective time indicators 318A and 318B and signal indicators 320A and 320B. The VSC 304 may also include a blank area 322 between the sub-graphs 316A and 316B. The blank area 322 may be configured to have notes or other messages displayed therein.

As shown in FIG. 3, the VSC 304 includes a first waveform 310 that is based on a first type of physiological signals and a second waveform 312 that is based on a second type of physiological signals. The first and second waveforms 310 and 312 are located in the first and second sub-graphs 316A and 316B, respectively. For example, the first waveform 310 may correspond to a fetal heart rate and the second waveform 312 may correspond to intrauterine pressure. In alternative embodiments, the VSC 304 may show more than two waveforms. Optionally, the VSC 304 could display a third waveform that corresponds to other physiological signals (e.g., fetal heart rate from another baby). Such embodiments may be used when a mother is pregnant with twins. In this optional case, the first and third waveforms may be offset from each other to visually distinguish the two waveforms. For example, the bottom of the two waveforms may be offset from the other by −60 bpm.

Also shown in FIG. 3, the VSC 304 may include a plurality of graph images 381-383. In the exemplary embodiment, the graph images 381-383 are identical and arranged side-by-side in the chart portion 302. Furthermore, the graph images 381-383 may include portions of the sub-graph 316A and 316B. Accordingly, each of the graph images 381-383 includes the time and signal indicators 318 and 320 from both sub-graphs 316A and 316B. In the illustrated embodiment, the sub-graph 316A has an aspect ratio defined by a time interval $\Delta t_2$ and a signal interval $\Delta s_2$, and the sub-graph 316B has an aspect ratio defined by a time interval $\Delta t_3$ and a signal interval $\Delta s_3$. In the illustrated embodiment, the time intervals $\Delta t_2$ and $\Delta t_3$ are equal, but the signal intervals $\Delta s_2$ and $\Delta s_3$ are not equal.

Thus, in some embodiments, the first and second waveforms 310 and 312 may be temporally synchronized such that the first and second waveforms 310 and 312 have the same time intervals and have a fixed relationship with respect to each other. Each time point in the virtual graph 314 may have a corresponding data point for the waveform 310 and a corresponding data point for the waveform 312. In this manner, a user may monitor the physiological signals for a mother and baby (or babies).

Embodiments described herein may include VSC's that are configured to include user-generated annotations or system-generated notices that are overlaid onto the virtual graph. The annotations and notices may facilitate analyzing and/or displaying the physiological information. Furthermore, the annotations and notices may be stored and recalled with the virtual graphs and waveforms. For example, as shown in FIG. 3, the VSC 304 may include a user-generated annotation 330. The user-generated annotation 330 may include limit indicators 332 and 334. In the illustrated embodiment, the limit indicators 332 and 334 are parallel dashed lines that are spaced apart and extend horizontally across the sub-graph 316A. Based on the scaling shown in FIG. 3, the dashed lines are separated by approximately 10 bpm. The annotation 330 may be generated based on user inputs. For example, a user may add the annotation 330 to the VSC 304 to facilitate determining an average movement or trend of the waveform over an extended period of time. More specifically, the user may set the limit indicator 332 at an identified peak of the waveform 310 and set the limit indicator 334 at an identified baseline of the waveform 310. The user may then review a history of the waveform 310 to determine how the physiological signals have changed over an extended period of time relative to the limit indicators 332 and 334.

FIG. 4 shows the viewable area 300 and illustrates user-generated annotations 340 and 350 and a system-generated notice 360. The annotation 340 may comprise a shaded (or colored) band or zone. The annotation 340 may be provided by, for example, a clinician to indicate where the waveform 310 should be located. For instance, upon reviewing the VSC 304, the clinician may determine that a "safe" range for the fetal heart rate extends approximately between 90-120 bpm. If the waveform 310 (i.e., fetal heart rate) moves outside of this range, the system may generate an alarm to notify the clinician or other user. Accordingly, the annotation 340 may be defined by alarm limits. If the waveform exceeds the upper alarm limit (120 bpm) or is less than the lower alarm limit (90 bpm), the user of the system may be notified. For example, the system may generate an audible noise that is heard in the room of the patient or in another remote room (e.g., nurse's station) or the system may page or somehow electronically notify the user.

The annotation 350 may be located in the blank area 322. The annotation 350 may include text provided by a user of the system. The text may be used to inform the user, such as one who subsequently reviews the VSC 304, that an event occurred at the noted time. For example, the annotation 350 may be text that states "changed patient position" or "provided medication." The text may provide information that explains why the waveform 310 and/or 312 changed or if the patient responded at all to an event.

The notice 360 may be a vertical bar or line that extends across the entire sub-graph 316A. The system can automatically generate the notice 360 after a predetermined period of time (e.g., every five minutes, ten minutes) or after the system identifies a pattern-of-interest in the waveform(s) 310 and/or 312. For example, the system may determine (e.g., through an analysis module, such as the analysis module 123) that the waveform 310 exceeded the upper alarm limit of the user selected annotation 340. The system analyzes the waveforms 310 and 312 using the analysis module to determine whether the event is concerning. If the event is determined to be benign, the notice 360 is colored green or some other color. If the event is determined to be concerning or requiring analysis by the user, the notice 360 may be colored red (or another color). The notice 360 and the annotations 330, 340, and 350 may be stored with the waveforms 310 and 312 and the virtual graph 314. As such, when reviewing the history of the VSC 304, a user could review the waveforms 310 and 312 and the virtual graph 314 in addition to any notes made by a user or any notices provided by the system.

FIG. 5 is a summary report 370 that may also be automatically generated by the system. The summary report 370 may be generated periodically or when requested by the user. The summary report 370 may be displayed (e.g., in the viewable area 300) or the summary report 370 may be automatically printed or sent electronically to a user of the system (e.g., via text or email). The summary report 370 may include rows and columns with cells having information that summarize a health of a patient at the time that the summary report 370 was generated. For example, the summary report 370 may include rows that provide information regarding (A) a health risk of the patient; (B) the patient's contractions; (C) a baseline rate; (D) variability in the rate; (E) whether accelerations are present; (F) whether decelerations are present; and (G) an overall assessment and action plan. The summary report may include spaces for user to enter comments regarding the information.

Figure 8:
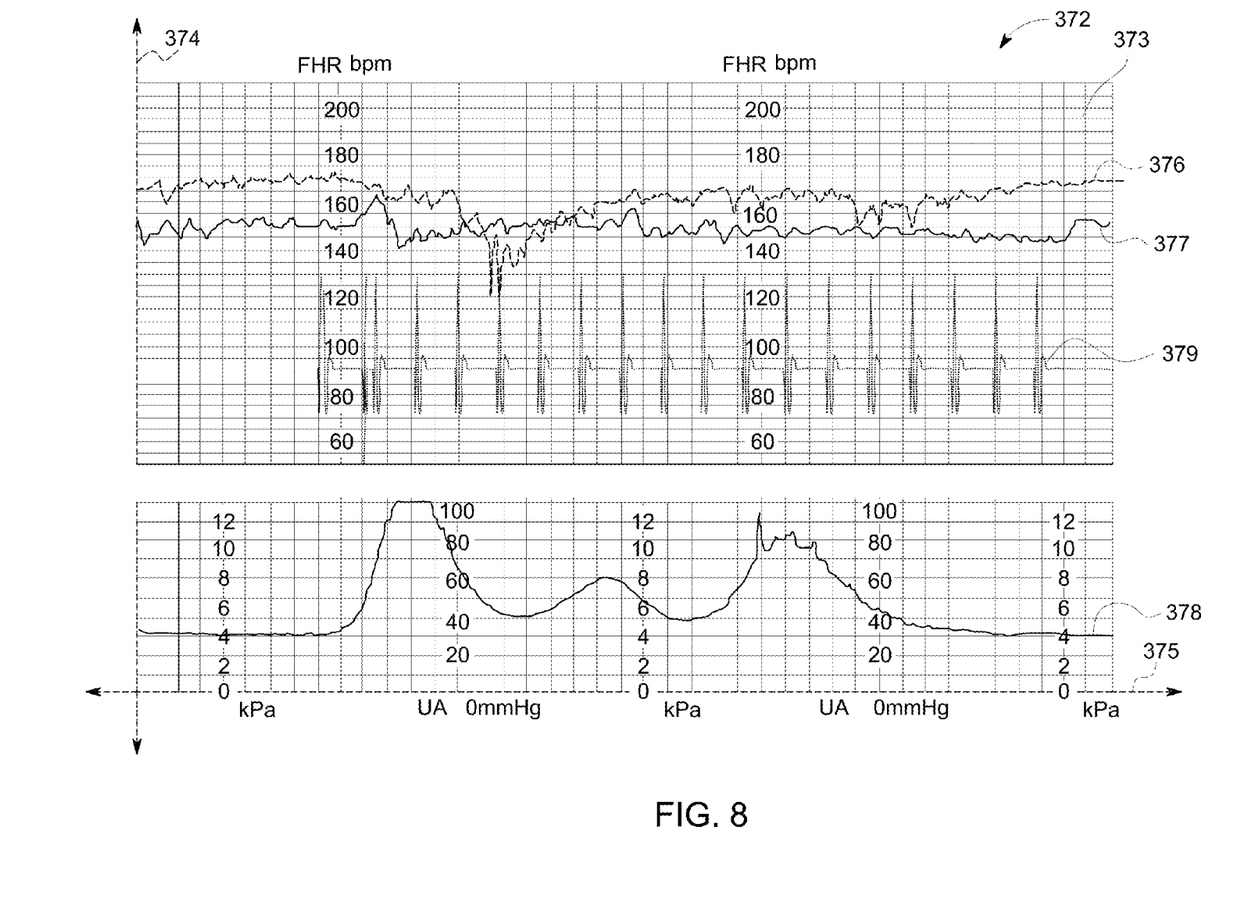
FIG. 8 illustrates a VSC formed in accordance with another embodiment having an additional waveform superimposed thereon.
Figure 9:
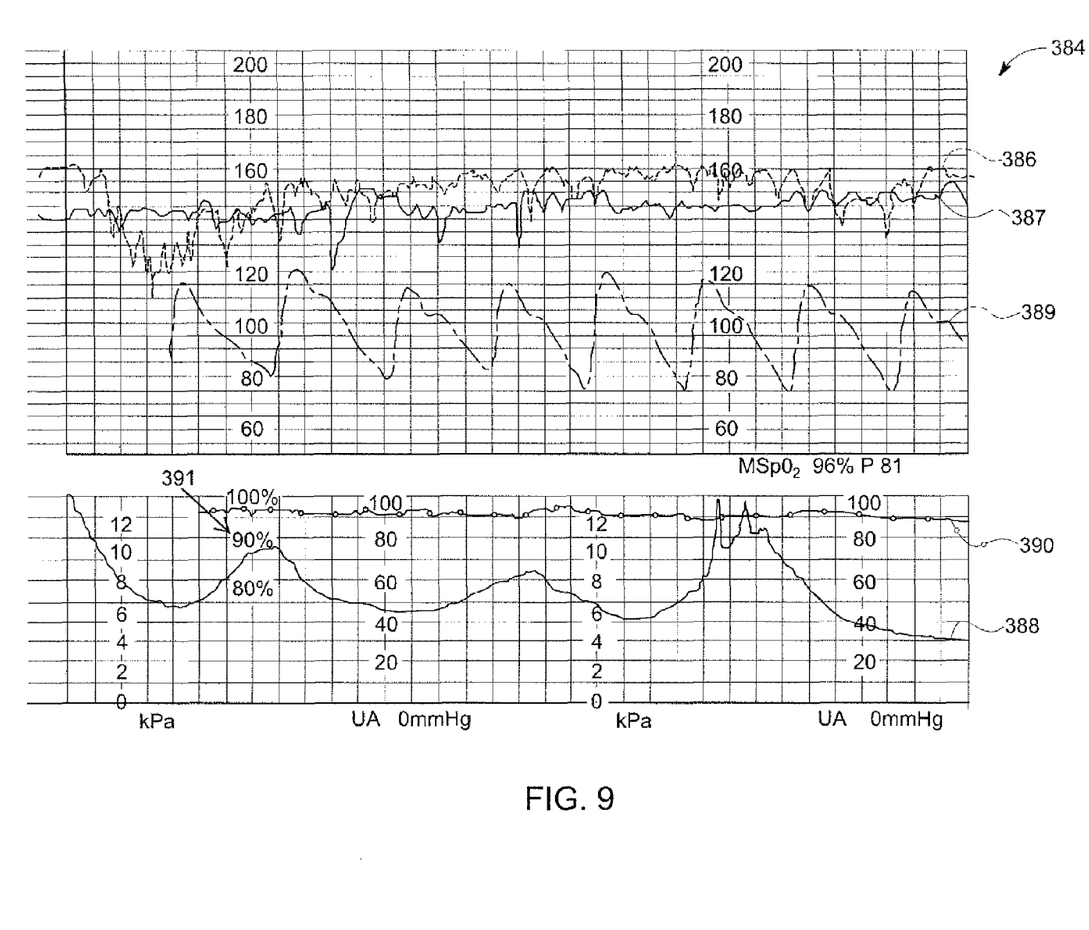
FIG. 9 illustrates a VSC formed in accordance with another embodiment having additional waveforms superimposed thereon.

FIGS. 8-9 illustrate VSCs 372 and 384, respectively, that may be shown in chart portions and viewable areas as described above. In some embodiments, the VSCs described herein may include superimposed waveforms that are not related to the time and/or the signal dimensions of other waveforms in the VSCs. For example, the VSC 372 includes a virtual graph 373 that may be similar to the virtual graphs described above. The virtual graph 373 includes time and signal dimensions 374 and 375. Similar to the VSCs described above, the VSC 372 includes waveforms 376 and 377 that correspond to the fetal heart rates of twin babies and a waveform 378 that corresponds to the intrauterine pressure of the mother. The VSC 372 also includes a waveform 379 that corresponds to the electrocardiogram of one of the babies (also referred to as a FECG). The waveform 379 may occur generally around the time that the waveforms 376-378 occur.

The shape or path of the waveform 379 may be based upon physiological signals obtained through the sensors 110 (FIG. 1) that are attached to the patient. The waveform 379 is superimposed onto the virtual graph 373. More specifically, the shape or path of the waveform 379 is not based on the time and signal dimensions 374 and 375. For example, the waveform 379 may be similar to waveforms that are typically provided for electrocardiograms in which the signal dimensions relate to voltage and the time dimension is typically different than the time dimension of a fetal heart rate. Thus, the features of the waveform 379 may be provided according to an established standard that is unrelated to the standard used for the waveforms 376 and 377.

The waveform 379 may be provided by the waveform module 121 (FIG. 1). The system 100 may receive user inputs through the input device 108 (FIG. 1) to select and add the waveform 379 to the VSC 372. For the time period in which the waveform 379 is obtained, the waveform 379 may be added to the virtual graph 373. Similar to other waveforms described above, positions of the data points of the waveform 379 may be saved with respect to the time and signal indicators (or other waveforms) of the virtual graph 373 such that the waveform 379 moves with the virtual graph 373. Accordingly, although the waveform 379 may occur generally around the time that the waveforms 376-378 occur, there is not a direct temporal relationship between the physiological signals represented by the waveform 379 and physiological signals represented by the waveforms 376-378. Nonetheless, a clinician may obtain information about the health of the patient through superimposed waveforms, such as the waveform 379.

FIG. 9 illustrates another example of superimposed waveforms. More specifically, the VSC 384 includes waveforms 386-388 that are similar to the waveforms 376-378 described above. In addition, the VSC 384 may include waveforms 389 and 390. The waveform 390 may relate to maternal saturation of peripheral oxygen ($MSpO_2$), the waveform 389 may correspond to a snapshot of maternal $SpO_2$ plethysmographic signals. In some embodiments, as shown with respect to the waveform 390, the VSC 384 may include superimposed signal indicators 391 (shown as 100%, 90%, and 80% in FIG. 9). The superimposed signal indicators 391 may be provided only when the waveform 390 is provided. The time dimension for the waveform 390 may be the same as the time dimension for the waveform 388. However, the waveform 389 does not have the same aspect ratio that is used with respect to the waveforms 386 and 387. For example, the waveform 389 is recorded at mm/s higher than the waveforms 386 and 387. However, the waveform 389 may be illustrated at an established standard typically analyzed by clinicians.

The above are only examples of superimposed waveforms included in VSCs. Other superimposed waveforms may be used. For example, the heart rate of the mother may be added to the VSC. Although the time dimension of this alternative waveform may be the same rate as the fetal heart rate, the beats/minute values may be different. Superimposed signal indicators could be added to the virtual graph in this case to facilitate understanding of the waveform.

Figure 6:
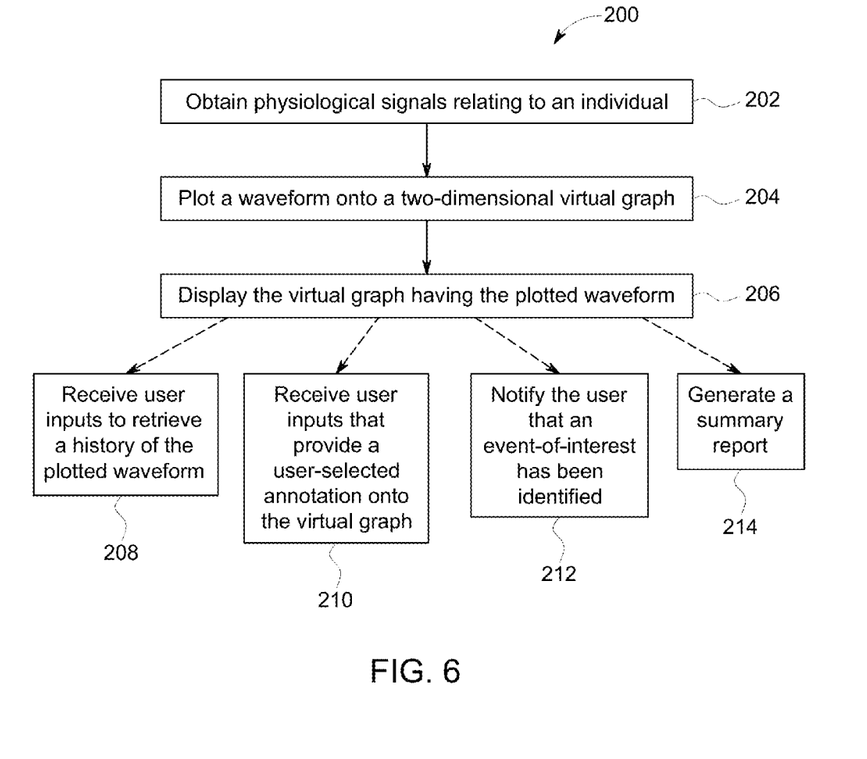
FIG. 6 is a block diagram illustrating a method for displaying waveform information.

FIG. 6 is a block diagram illustrating a method 200 of displaying physiological information in accordance with one embodiment. Although the following is with respect to physiological signals, the method 200 may similarly be performed with other waveform signals. The method 200 may be carried out or performed by, for example, the system 100 (FIG. 1). The method 200 includes obtaining at 202 physiological signals. The physiological signals may relate to an individual (e.g., patient) that may be an animal or human. For example, the physiological signals may relate to an intrauterine pressure or fetal heart rate. In some embodiments, the physiological signals are obtained directly from a patient in real-time through sensors. In other embodiments, the physiological signals may be obtained through a local or remote database.

The method 200 also includes plotting at 204 a waveform onto a two-dimensional virtual graph having a time dimension and a signal dimension. In some embodiments, the virtual graph having the waveform plotted therein may constitute a VSC as described above. The waveform may be provided, for example, by the waveform module 121 (FIG. 1). The virtual graph may be provided by the graph module 122 and include one or more graph images in the viewable area as described above. The graph images may be identical so that only one graph image is stored by the system. The virtual graph may also include visual indicators, such as signal indicators and time indicators. The visual indicators may have a predetermined pattern along the virtual graph to facilitate analysis by the user. For example, the visual indicators may be patterned at a predetermined aspect ratio. The aspect ratio of the virtual graph may be consistent with established standards for similar paper strip charts, such as the U.S. or international standards for cardiotocography.

The method 200 also includes displaying at 206 the virtual graph having the plotted waveform thereon in a chart portion of a viewable area. The viewable area may be part of a display of the user interface. The visual indicators of the virtual graph may shift along the viewable area at a recording speed as the waveform is plotted. The plotted waveform may have a fixed relationship with respect to the visual indicators and shift at the recording speed.

Optionally, the method 200 may include receiving at 208 user inputs to retrieve a history of the plotted waveform. For example, the user may communicate to the system that the user would like to review that past 20 minutes of recorded waveform signals. Upon receiving the user inputs, the plotted waveform may be retrieved. The plotted waveform may begin moving from the selected time. In some embodiments, the user may use a touchscreen that allows the user to scroll back and forth through the history. For example, the system may allow the user to review a history of the physiological signals at a rate that is faster than the recording speed.

Also optionally, the method 200 may include receiving at 210 user inputs to provide a user-generated annotation onto the virtual graph. The annotations may be similar to the annotations 330, 340, and 350. The annotations may be stored by the system so that the annotations may be retrieved along with the plotted waveform and the virtual graph. The method may also include notifying at 212 the user that an event-of-interest has been identified by the system. For example, the system may identify a predetermined pattern that is associated with an event-of-interest. The system may then notify the user that a possible event-of-interest has occurred. The method may also include generating at 214 a summary report of the physiological signals as described above.

Figure 7:
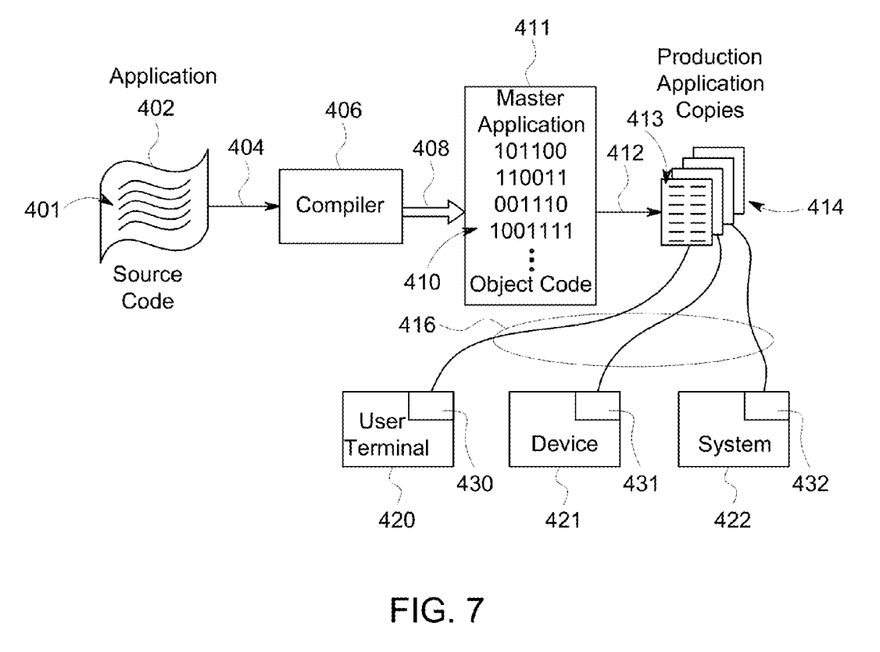
FIG. 7 is a block diagram of exemplary manners in which various embodiments described herein may be stored, distributed, and installed on computer readable medium.

FIG. 7 is a block diagram of exemplary manners in which various embodiments described herein may be stored, distributed, and installed on computer readable medium. In FIG. 7, an "application" represents one or more of the methods and process operations discussed above. As shown in FIG. 7, the application is initially generated and stored as source code 401 on a source computer readable medium 402. The source code 401 is then conveyed over path 404 and processed by a compiler 406 to produce object code 410. The object code 410 is conveyed over path 408 and saved as one or more application masters on a master computer readable medium 411. The object code 410 is then copied numerous times, as denoted by path 412, to produce production application copies 413 that are saved on separate production computer readable medium 414. The production computer readable medium 414 is then conveyed, as denoted by path 416, to various systems, devices, terminals and the like. In the example of FIG. 7, a user terminal 420, a system 421 and a system 422 are shown as examples of hardware components, on which the production computer readable medium 414 are installed as applications (as denoted by 430-432).

The source code may be written as scripts, compiled, or in any high-level or low-level language. Examples of the source, master, and production computer readable medium 402, 411, and 414 include, but are not limited to, CDROM, RAM, ROM, Flash memory, RAID drives, memory on a computing system and the like. Examples of the paths 404, 408, 412, and 416 include, but are not limited to, network paths, the internet, Bluetooth, GSM, infrared wireless LANs, HIPERLAN, 3 G, satellite, and the like. The paths 404, 408, 412, and 416 may also represent public or private carrier services that transport one or more physical copies of the source, master, or production computer readable medium 402, 411, or 414 between two geographic locations. The paths 404, 408, 412, and 416 may represent threads carried out by one or more processors in parallel. For example, one computer may hold the source code 401, compiler 406 and object code 410. Multiple computers may operate in parallel to produce the production application copies 413. The paths 404, 408, 412, and 416 may be intra-state, inter-state, intra-country, inter-country, intra-continental, inter-continental and the like.

The phrases "computer readable medium" and "instructions configured to" shall refer to any one or all of i) the source computer readable medium 402 and source code 401, ii) the master computer readable medium and object code 410, iii) the production computer readable medium 414 and production application copies 413 and/or iv) the applications 430-432 saved in memory in the terminal 420, system 421 and system 422.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is complied to run on both 32-bit and 64-bit operating systems. A 32-bit operating system like Windows XP™ can only use up to 3 GB bytes of memory, while a 64-bit operating system like Window's Vista™ or 7™ can use as many as 16 exabytes (16 billion GB).

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

At least one technical effect of various embodiments includes displaying physiological information in a virtual manner that may be reviewed and analyzed by a user. Another technical effect includes displaying physiological information that is similar to established display standards of strip paper charts so that the user may quickly review and analyze the physiological information. Another technical effect includes storing a history of the physiological signals so that a user may retrieve or recall the physiological signals to review at least a portion of the time that the physiological signals were obtained.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for displaying physiological information, the system comprising:
    a user interface having a viewable chart portion configured to display physiological information of an individual;
    a graph module configured to provide a two-dimensional virtual graph having a time dimension and a signal dimension, the virtual graph including time indicators that are spaced along the time dimension indicating time intervals and signal indicators that are spaced along the signal dimension indicating a predetermined signal scaling; and
    a waveform module configured to obtain physiological signals as a function of time, the waveform module configured to plot a waveform that is based upon the physiological signals on the virtual graph;
    wherein the user interface is configured to display the waveform and the virtual graph in the chart portion, the time and signal indicators of the virtual graph shifting along the time dimension in the chart portion at a recording speed as the waveform is plotted, the plotted waveform having a fixed relationship with respect to the time and signal indicators and shifting at the recording speed, the waveform module configured to store a history of the waveform extending out of a viewable area of the chart portion; and
    wherein the user interface is configured to receive a first user input for displaying a reference indicator on the virtual graph, the reference indicator extending along the time dimension and representing a signal value designated by the first user input, the user interface configured to subsequently receive a second user input for retrieving the history of the waveform into the chart portion to enable a user to view the retrieved history of the waveform relative to the reference indicator at the designated signal value.

2. The system in accordance with claim 1, wherein the virtual graph comprises at least one graph image that covers an area of the chart portion, the at least one graph image having a fixed relationship with respect to the plotted waveform, wherein the at least one graph image shifts in a first direction along the time dimension when a new data point of the waveform is plotted.

3. The system in accordance with claim 1, wherein the virtual graph comprises first and second graph images having the time and signal indicators, the first and second graph images being arranged so that the time intervals are substantially uniform across the chart portion, the plotted waveform having a fixed relationship with respect to the first and second graph images while shifting at the recording speed.

4. The system in accordance with claim 1, further comprising sensors communicatively coupled to the waveform module, the sensors configured to detect the physiological signals from the individual.

5. The system in accordance with claim 1, further comprising an analysis module, the analysis module configured to identify predetermined patterns of the waveform that are indicative of an event-of-interest, the analysis module configured to notify the user that the event-of-interest occurred.

6. The system in accordance with claim 1, wherein the physiological signals comprise physiological signals of a first type, and the waveform comprises a first waveform, wherein the user interface is configured to display a second waveform that is based upon physiological signals of a second type, the first and second waveforms being synchronized in the chart portion such that the first and second waveforms have a fixed relationship with respect to each other.

7. The system in accordance with claim 6, wherein the physiological signals of the first type indicate a fetal heart rate and the physiological signals of the second type indicate intrauterine pressure, the chart portion having a viewable blank area that separates the virtual graph into first and second sub-graphs that include the first and second waveforms, respectively, the blank area configured to receive a textual message from a third user input associated with a designated time.

8. The system in accordance with claim 6, wherein the user interface is configured to superimpose the second waveform on the virtual graph over the time and signal indicators of the first waveform, the second waveform being offset from the first waveform on the virtual graph along the signal dimension.

9. The system in accordance with claim 1, wherein the physiological signals relate to a heart rate, body temperature, blood pressure, respiratory rate, electrical activity, or intrauterine pressure.

10. The system in accordance with claim 1, wherein, in response to the second user input, the user interface is configured to scroll the virtual graph and the waveform, as the waveform is being plotted, in a direction that is opposite a plotting direction so that the history of the waveform is retrieved into the chart portion and so that the retrieved history is viewable relative to the reference indicator.

11. The system in accordance with claim 1, wherein the reference indicator includes a pair of limit indicators that are spaced apart along the signal dimension by a designated signal value, the limit indicators being lines that extend along the time dimension.

12. The system in accordance with claim 1, wherein the user interface is configured to receive a third user input for entering a textual message into the chart portion that is associated with a designated time.

13. The system in accordance with claim 12, wherein the chart portion includes a viewable blank area that is distinct from the waveform and the virtual graph, the textual message being located within the blank area and moving within the blank area when the textual message moves with the waveform.

14. The system in accordance with claim 1, wherein the user interface is configured to display a notice indicator extending along the signal dimension and representing a time at which an event-of-interest occurred, the event-of-interest being automatically determined by the system, the notice indicator indicating whether the event-of-interest is benign or concerning, the notice indicator being stored and retrieved into the chart portion when the history of the waveform is retrieved.

15. The system in accordance with claim 1, wherein the waveform is a first waveform, wherein the user interface is configured to display a second waveform and a third waveform on the virtual graph over the time and signal indicators of the first waveform, the first waveform indicating intrauterine pressure of a mother and the second and third waveforms indicating fetal heart rates of two babies in the mother, the second waveform being offset from the third waveform on the virtual graph along the signal dimension.

16. A method for displaying waveform information, the method comprising:
obtaining waveform signals as a function of time;
plotting a waveform onto a two-dimensional virtual graph having a time dimension and a signal dimension, the virtual graph including time indicators that are spaced along the time dimension and indicate time intervals, the virtual graph also including signal indicators that are spaced along the signal dimension and indicate a predetermined signal scaling;
displaying the virtual graph and the plotted waveform in a chart portion of a user interface, the time and signal indicators of the virtual graph shifting along the chart portion at a recording speed as the waveform is plotted, the plotted waveform having a fixed relationship with respect to the time and signal indicators and shifting at the recording speed, wherein a history of the waveform extending out of a viewable area of the chart portion is stored;
receiving a first user input for displaying a reference indicator on the virtual graph, the reference indicator extending along the time dimension and representing a signal value designated by the first user input; and
receiving a second user input, as the waveform is being plotted, for scrolling the history of the waveform into the chart portion along the time dimension to enable a user to view the history of the waveform relative to the reference indicator at the designated signal value as the waveform moves along the time dimension.

17. The method in accordance with claim 16, wherein the virtual graph comprises at least one graph image that covers an area of the chart portion, the at least one graph image having a fixed relationship with respect to the plotted waveform when displayed, wherein the at least one graph image shifts in a first direction along the time dimension when a new data point of the waveform is plotted.

18. The method in accordance with claim 16, wherein the virtual graph comprises first and second graph images having the time and signal indicators, the first and second graph images being arranged so that the time intervals are substantially uniform across the chart portion, the plotted waveform having a fixed relationship with respect to the first and second graph images while shifting at the recording speed.

* * * * *